United States Patent [19]

Katinger et al.

[11] Patent Number: 5,246,855
[45] Date of Patent: Sep. 21, 1993

[54] REACTOR FOR CARRYING OUT BIOLOGICAL REACTIONS BY MEANS OF BIOCATALYSTS

[75] Inventors: Hermann W. D. Katinger; Manfred Reiter; Gerald Blüml; Nicolaus Zach; Theodor Gaida, all of Vienna, Austria

[73] Assignee: Vogelbusch Gesellschaft m.b.H., Austria

[21] Appl. No.: 660,696

[22] Filed: Feb. 25, 1991

[30] Foreign Application Priority Data

Jan. 16, 1991 [AT] Austria ..................... 93/91

[51] Int. Cl.⁵ .................. C12M 1/36; C12M 1/14; C12M 1/08
[52] U.S. Cl. ................... 435/289; 435/310; 435/314; 435/316; 435/813
[58] Field of Search ................ 435/284–286, 435/288, 289, 290, 291, 299, 310, 311, 313–316, 813, 818; 422/140, 224, 225, 227, 269, 274; 210/150, 151, 615–617, 629, 263; 366/101–103, 106, 107; 261/122

[56] References Cited

U.S. PATENT DOCUMENTS

| | | | |
|---|---|---|---|
| 2,111,726 | 3/1938 | Plews | 435/314 |
| 3,288,567 | 11/1966 | Graham | 422/140 |
| 3,523,763 | 8/1970 | Driesen et al. | 422/140 |
| 4,202,774 | 5/1980 | Kos | 210/274 |
| 4,545,909 | 10/1985 | Atkinson et al. | 435/285 |
| 4,782,024 | 11/1988 | Scott et al. | 435/313 |
| 4,789,634 | 12/1988 | Muller-Lierheim et al. | 435/285 |
| 4,891,318 | 1/1990 | Oosterhuis et al. | 435/315 |
| 4,935,348 | 6/1990 | Oosterhuis et al. | 435/813 |
| 5,043,283 | 8/1991 | Endo et al. | 435/313 |

FOREIGN PATENT DOCUMENTS

| | | | |
|---|---|---|---|
| 0095804 | 12/1983 | European Pat. Off. | |
| 3422012 | 12/1984 | Fed. Rep. of Germany | 422/140 |
| 0147229 | 8/1985 | Japan | 422/140 |
| WO8605202 | 9/1986 | PCT Int'l Appl. | |
| WO9011345 | 10/1990 | PCT Int'l Appl. | |
| 525959 | 9/1972 | Switzerland | |
| 1417487 | 12/1974 | United Kingdom | 435/313 |

OTHER PUBLICATIONS

Hsu et al. "Oxygen Transfer to Mixed Cultures in Tower Systems" Biotech and Bioeng. vol. XVII (1975) pp. 499–514.

Primary Examiner—Michael G. Wityshyn
Assistant Examiner—William H. Beisner
Attorney, Agent, or Firm—Henry M. Feiereisen

[57] ABSTRACT

A reactor for carrying out biological reactions by means of biocatalysts includes a base which houses an agitator unit and suitable monitor and control devices and a securely attachable lid. Interposed between the lid and the base is an intermediate part in form of a vat which for application as fluid-bed reactor and/or fixed-bed reactor includes at its lower end a gas bubbles-permeable support for a biocatalyst-laden matrix or biocatalyst matrix. Extending from the upper area of the intermediate part toward the base is a circulation line which cooperates with the agitator unit which is designed as circulating pump.

14 Claims, 3 Drawing Sheets

REACTOR FOR CARRYING OUT BIOLOGICAL REACTIONS BY MEANS OF BIOCATALYSTS

BACKGROUND OF THE INVENTION

The present invention refers to a reactor for carrying out biological reactions by means of biocatalysts, and in particular to a bioreactor of the type having a base which houses an agitator unit, monitor and control devices and is tightly sealable by a lid.

Bioreactors of this type are suitable for batchwise or continuous operation, with the biocatalysts being discharged together with the substrate which is subsequently separated.

Other reactors are known in which the biocatalysts are immobilized on a carrier matrix, e.g. so-called "microcarriers" or form themselves a separate matrix through agglomeration, with the microcarrier or the matrix of biocatalysts being arranged in a cylinder through which substrate flows from below to thereby fluidize the microcarrier or matrix of biocatalysts in form of a fluidized bed. When the substrate flows through the matrix or the microcarrier, the specific weight thereof and the synchronized flow velocity allows the microcarrier or the matrix to remain in the cylinder while the transformed substrate is withdrawn from the upper end and returned to the circulation. The circulation line is connected to a gas exchanger in which the substrate is enriched with oxygen and the formed carbon dioxide is withdrawn. Additionally connected to the circulation line are heating elements, pH measuring elements, oxygen sensors, temperature sensors and a circulation pump. Such designs have the disadvantage that oxygen can be introduced into the substrate only to a degree as can be dissolved therein so that the oxygen concentration within the fluidized bed drops considerably and the oxygen portion of the substrate in the upper area of the fluidized bed is so low as to mar the further reaction.

SUMMARY OF THE INVENTION

It is a general object of the present invention to provide an improved bioreactor for carrying out biological reaction by means of biocatalysts obviating the aforestated drawbacks.

In particular, it is an object of the present invention to provide a bioreactor of the above-mentioned type which provides over its entire length a sufficient amount of reaction gas for the biocatalysts.

These objects, and others, which will become apparent hereinafter are attained in accordance with the present invention by providing between the base and the lid an intermediate part in form of a vat which for application as fluidized bed reactor and/or fixed bed reactor includes at its lower area a gas bubbles permeable support, especially support plate for a biocatalyst-laden matrix or biocatalyst matrix, and by providing a circulation line which extends from the upper area of the intermediate part toward the base, with the agitator unit being designed as circulating pump.

Through the provision of a bioreactor in accordance with the invention, the introduced gas bubbles can penetrate the support plate so that bubble-like gas can enter the fluidized bed or fixed bed, whereby the gas bubbles during their flow through the carrier matrix or biocatalyst matrix continuously create new interfaces between the bubble content and the substrate to thereby accomplish a complete utilization of the introduced gas bubbles. Further, the creation of interfaces allows a gas exchange so that oxygen may escape from the bubbles while the metabolite carbon dioxide can be discharged from the system.

A further advantage of the present invention resides in the fact that a conventional reactor can be modified into a fluidized bed reactor or fixed-bed reactor, whereby monitor and control devices as employed in conventional reactor can be used with the fluidized bed reactor.

Advantageously, the intermediate part is designed in modular system so that expensive equipment of the base for a number of reactor types are usable.

According to another feature of the present invention, the support plate has a hydrophobic surface and a permeability in the range of 3 to 12%, preferably 5 to 7.5% so as to permit air bubbles to flow past the support plate unimpeded without formation of large bubbles at the underside which may erupt during penetration through the support plate to thereby upwardly entrain the biocatalyst-laden matrix or biocatalyst matrix. In order to create a superior gas introduction, the gas bubbles-permeable support may be designed as static mixer to thereby attain a repeated thorough mixing of the reactor liquid with the gas.

Suitably, the circulation line may be designed as a central pipe which may be closed by a grid and extends through the support plate toward the agitator unit. The provision of such a centrally located circulation line not only avoids energy losses which were encountered by externally mounted pipes but also reduces the demand on space. Moreover, the reactor in accordance with the present invention is especially easy to sterilize and to clean.

In order to enhance the pump action of the agitator unit, the central circulation line is provided at its lower end with a cylindrical collar or dome which encloses the pump-forming impeller of the agitator unit, with the agitator unit being designed as axial conveyor. Thus, a superior circulation is attained, and by centrally drawing the liquid from the lower end of the collar, a particular even circulation is created. Preferably, a flared transition connects the circulation line and the collar to thereby create superior fluidic conditions.

According to yet another feature of the present invention, the impeller is arranged approximately in the central axis of the collar to create a same effective pump action in both directions.

For preventing a rotation of reactor liquid during rotation of the impeller and for deflecting the reactor liquid vertically upwards and evenly through the support plate, suitable baffles may be provided within the collar and in a space between the collar and the inner wall surface of the base. Thus, the flow is even from bottom to top so that uniform flow conditions are created in the fluidized bed or fixed bed.

Suitably, the wall of the circulation line is designed at least along some sections thereof as filter membrane, e.g. ultrafiltration membrane, or as permeation membrane for allowing cleaning and similar processes during circulation.

Gas supply elements may also be provided in the circulation line above the agitator unit, especially in the flared transition, to provide an especially effective gas introduction. Thus, the introduced gas is instantly finely divided in the liquid and subsequently fed as finely divided bubbles through the support plate into the fluidized bed or fixed bed.

Preferably, the impeller of the agitator unit is designed to be low of shearing forces so that cells in suspension can survive and can be returned to the matrix without encountering lysis products which e.g. could be attributed to mechanical damage of the cells through the agitator unit.

Suitably, the direction of rotation of the agitator unit may be reversible so that a compact packing of the fluidized bed or fixed bed and a good inoculation through backflushing are attainable.

BRIEF DESCRIPTION OF THE DRAWING

The above and other objects, features and advantages of the present invention will now be described in more detail with reference to the accompanying drawing in which.

DETAILED DESCRIPTION OF A PREFERRED EMBODIMENT

Figure 1:
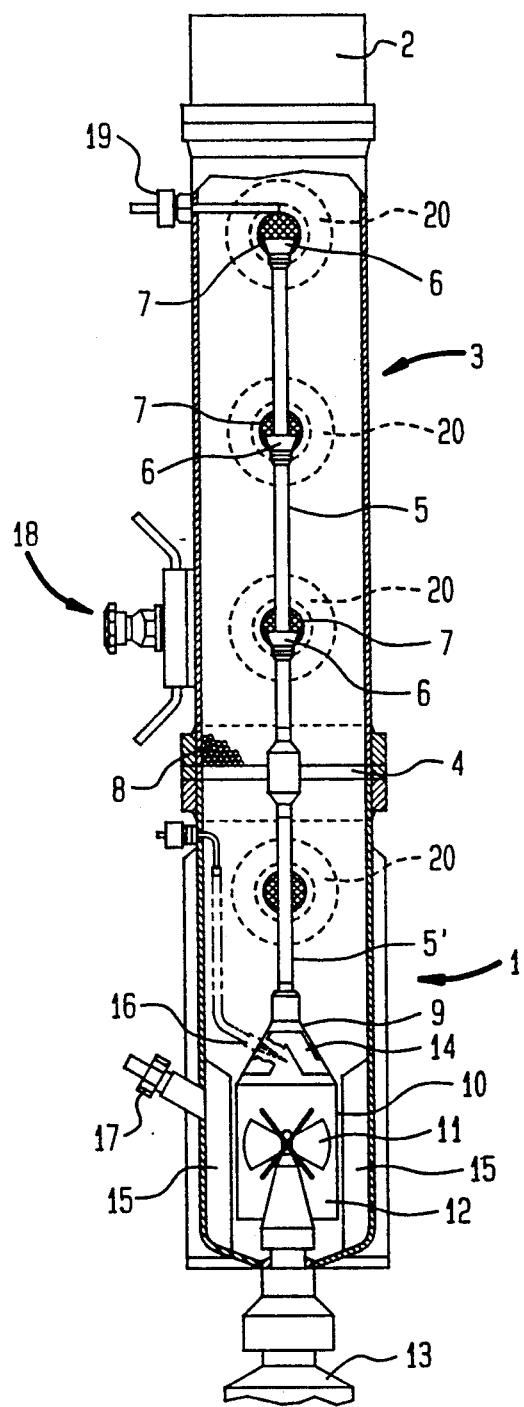
FIG. 1 is a schematic vertical section of one embodiment of a bioreactor in accordance with the present invention.

Referring now to the drawing, and in particular to FIG. 1, there is shown a schematic vertical section of one embodiment of a bioreactor in accordance with the present invention. The reactor includes a base generally designated by reference numeral 1 which is upwardly continued by an intermediate part in form of a vat generally designated by reference numeral 3 and being part of a modular system so as to be exchangeable with another intermediate part. As indicated in broken lines, the upper end of the intermediate part 3 is securely closable by a lid 2.

In the nonlimiting example, the intermediate part or vat 3 is configured for application as a fluidized reactor or fixed-bed reactor by mounting a porous support plate 4, e.g. via a bolted connection, to the lower end of the intermediate part 3. The support plate 4 is made of hydrophobic material and has a permeability of 3 to 12%. In the nonlimiting example of the bioreactor of FIG. 1, the permeability of the support plate 4 ranges from 5 to 7.5%.

The design of the support plate 4 allows its use as static mixer and the hydrophobic surface and the permeability renders the support plate 4 permeable for gas bubbles.

Contained in the intermediate part 3 and placed upon the support plate 4 is filling material which is indicated in FIG. 1 by reference numeral 8 and may be a carrier matrix for biocatalysts, so-called "microcarriers" of specific weight and suitable porous structure so that biocatalysts e.g. microorganism, cells of cell cultures, enzymatic chains and the like adhere to the microcarrier, or the microcarriers are overgrown with organisms. Alternatively, the bioreactor may be designed in such a manner that the utilized biocatalysts are so-called suspension cells, i.e. cells which adhere to the surface of the microcarrier solely based on mechanical interaction.

Extending through the intermediate part 3 is a central circulation line or pipe 5, with its upper end connected to a feed hopper 6 which is positioned in dependence on the filling level of filling material 8 within the bioreactor. For illustrative purposes, the nonlimiting example of FIG. 1 shows the feed hopper 6 at three different levels. The top of the feed hopper 6 is covered by a grid 7 in order to be free of vortex during aspiration and to prevent drawing of filling material 8 of the fixed bed or fluidized bed into the circulation line 5. Preferably, sections of the wall of the circulation line is designed as filter membrane e.g. ultrafiltration membrane or as permeation membrane.

As further shown in FIG. 1, the central circulation line 5 is extended into the base 1 by an extension line 5' which is connected at its lower end to a flared or conically widening transition 9. The lower end of the transition 9 is continued by a collar or cylindrical dome 10 which houses an impeller 11 of an agitator unit 12. The impeller 11 and the collar 10 define together an axial-flow pump, with the impeller 11 being adapted for operation in both conveying directions by means of a reversible electromotor 13. The interior of the flared transition 9 accommodates baffles 14 by which the liquid or broth (nutrient medium) is prevented from rotating within the collar 10 during operation of the impeller 11. Further baffles 15 are arranged in the area between the collar 10 and the wall of the base 1 for deflecting liquid exiting from the collar 10 to flow vertically upwards and evenly through the porous support plate 4.

In communication with the transition 9 is a gas supply line 16 by which finely divided gas is introduced to the flow of liquid flowing to the impeller 11. By means of the impeller 11, the gas is further divided so that the resulting superfinely divided gas subsequently enters the reactor from the lower end of the collar 10 together with the liquid and flows upwards with the liquid toward the porous support plate 4. Since the support plate 4 is hydrophobic, the gas bubbles pass through the support plate 4 without adhering thereto to thereby traverse the fluidized bed or fixed bed. By passing through the fluidized bed or fixed bed, the friction of the gas bubbles at the filling material 8 generates new gas exchange surfaces to thereby attain an increased gas/liquid mass transfer. Therefore, oxygen is continuously available in a sufficient amount even at the upper end of the bioreactor.

The base 1 of the bioreactor according to FIG. 1 is further provided with a connecting piece 17 adapted for attachment by a sample withdrawal device, measuring electrodes such as oxygen electrode, pH electrode or the like. Samples may also be withdrawn through a sample withdrawal device 18 which is mounted to the lower end of the intermediate part 3, or through a spare connection 19 which is mounted to the upper area of the intermediate part 3 and may also be used for introduction of gas. Flow conditions within the fluidized bed can be monitored through viewing glasses 20 which are provided at suitable locations as indicated in broken lines in FIG. 1.

In order to be able to use a bioreactor according to the present invention for growing even those cells which are partly washed out by the liquid flow and then returned to the bed by the circulation, the impeller 11 of the agitator unit 12 is low on shear forces i.e. there are no sharp impacting edges which may damage the cells, and the geometry of the impeller is defined to maximize the conveying capacity and to minimize turbulent and mechanical shearing effects.

The following examples describe the operation of the reactor in accordance with the present invention:

EXAMPLE 1

(Adherent Cell Type); Culture in Fluidized Bed Reactor

Example 1 describes the culture of an adherent animal cell line of an immunoglobulin G (IgG) secreting, recombinant Chinese Hamster Ovary (CHO) cell (source "Institut für angewandte Mikrobiologie der Universität für Bodenkultur" (IAM)) as typical case of a cell line which utilizes the growth and the retention of the metabolic activity on a carrier matrix upon which the cell line is preferably anchored.

In example 1, the recombinant CHO cells are cultivated with DMEM/HAM's F12 medium (Dulbecco's modified Eagle's medium) with 5% fetal calf serum at standard conditions in a 10 liter laboratory fluidized reactor with porous microcarriers.

Figure 2:
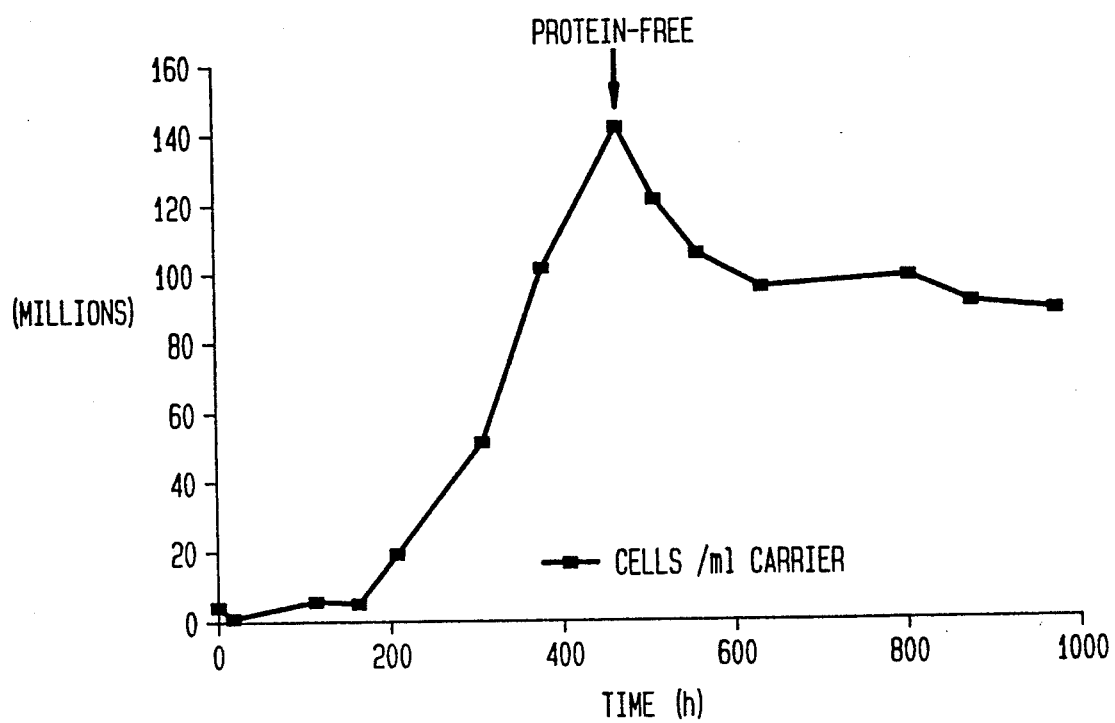
FIGS. 2-4 are each a graphical illustration of cell densities attained during the course of an exemplified test run.

FIG. 2 depicts a graphical illustration of the cell densities attained during the course of the test over a time period of 970 hours, with the vertical coordinate indicating the number of cells in millions and the horizontal coordinate indicating the duration of the test in hours. As depicted in FIG. 2, the maximum cell density attainable is $140 \times 10^6$ cells per milliliter of porous carrier matrix. The arrow pointing at test hour 466 refers to the use of a protein-free culture medium resulting only in slight impairment of growth and metabolism.

This example is representative for many standard cell lines like e.g. recombinant and non-recombinant CHO, baby hamster kidney cells (BHK), African green monkey kidney cells (VERO) etc.

EXAMPLE 2

(Type of a Suspension Cell); Culture in Fluidized Bed Reactor

Example 2 refers to the culture of a suspension cell line, a mouse/human hybrid (source IAM). The immortalization partner as well as the cells fused with this immortalization partner are cells of the lymphatic system which usually exist as cells suspended peripherally in the blood and serve as representatives for "suspension cells" in example 2.

In example 2, the suspension cells are cultivated with RPMI 1640 medium supplemented with 2% fetal calf serum at standard conditions (37° C., pH 6,95) on porous microcarriers in a 10 liter laboratory fluidized reactor.

Figure 3:
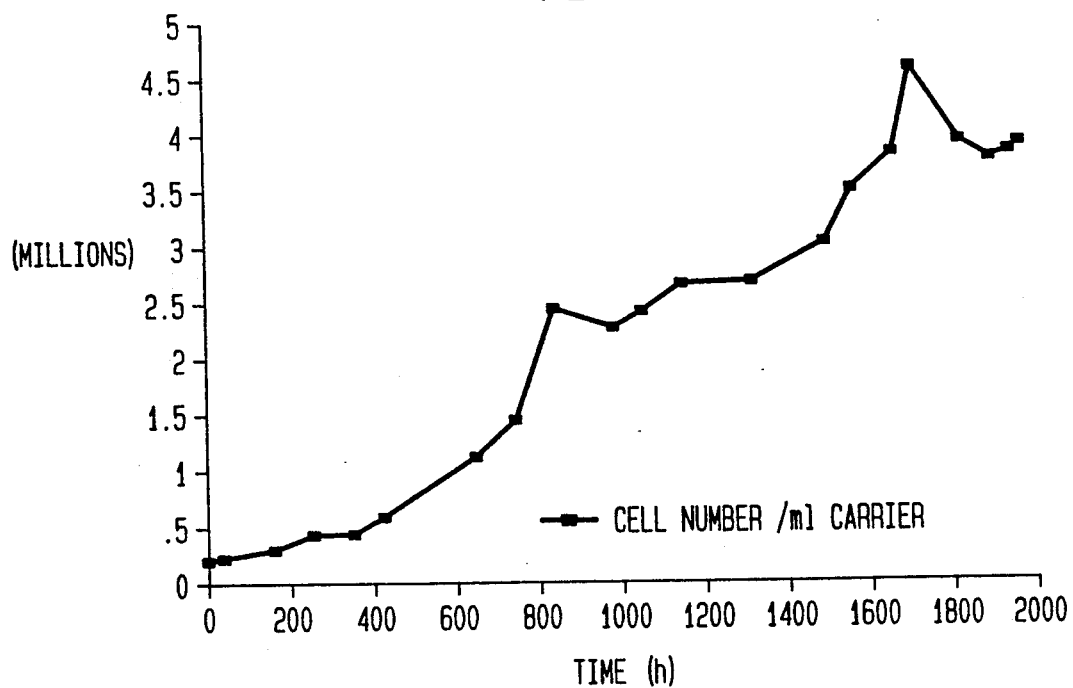

FIG. 3 depicts the obtained cell density over a time period of 2000 hours. The maximum cell density obtained is at $4.5 \times 10^6$ cells per milliliter porous carrier matrix. In comparison with conventional reactor types (chemostatic cultures), the cell densities obtained by the reactor in accordance with the present invention are increased by the factor 10 to 15.

Example 2 shows that with the fluidized reactor in accordance with the invention, even hybridom cells (human hybrids, xenohybrids) which grow at very slow pace and in low density, can be cultivated at high cell densities i.e. cell densities which considerably exceed $10^6$ hybrids per milliliter.

EXAMPLE 3

(Type of a Suspension Cell); Culture in Fixed-Bed Reactor (Packed Bed) and fluidized bed reactor respectively.

Example 3 refers to the culture of a suspension cell line (mouse×mouse hybridom cell line). In example 3, the suspension cells are cultivated with RPMI 1640 medium at standard conditions (37° C., pH 7) on porous microcarriers in a 10 liter laboratory fluidized bed reactor. During the first 200 hrs after inoculation, the reactor was used as a fixed-bed-reactor under reduced liquid circulation rate in order to promote cell attachment.

Figure 4:
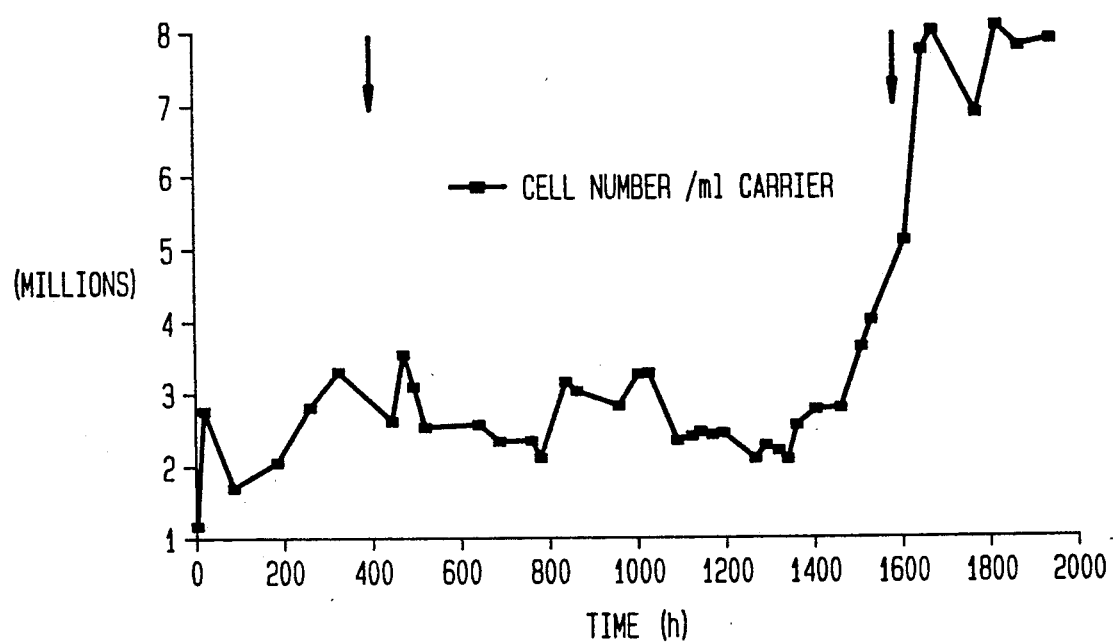

FIG. 4 depicts the obtained cell density over a time period of 2000 hours. The maximum cell density obtained is $8 \times 10^6$ cells per milliliter of porous carrier matrix. The arrows inserted at test hours 400 and 1600 refer to the use of serum-free perfusion medium during this time period. The illustration of FIG. 4 indicates that even when using a serum-free medium, the culture shows normal growth and unaltered metabolic activity over a wide range.

Example 4 shows that during cultivation of hybridom cells of murine origin (mouse×mouse hybridom cells) with the described fluidized be reactor or fixed-bed reactor, high cell densities can be accomplished i.e. cell densities which considerably exceed $5 \times 10^6$ cells per milliliter.

While the invention has been illustrated and described as embodied in a reactor for carrying out biological reactions by means of biocatalysts, it is not intended to be limited to the details shown since various modifications and structural changes may be made without departing in any way from the spirit of the present invention.

We claim:

1. A modular reactor for carrying out biological reactions by means of biocatalysts; comprising:
   a base having an interior space and defining an axis;
   a lid;
   an intermediate section adapted for providing a reaction zone, with said lid constructed so as to be detachably secured to said intermediate section, said intermediate section being constructed so as to be detachably secured between said base and said lid and including a gas bubbles-permeable support member at the junction to said base, said intermediate section being part of a modular kit so as to be replaceable by another intermediate section for allowing selective application of the reactor as a fluidized bed reactor and fixed bed reactor;
   a carrier matrix contained in the reaction zone within said intermediate section above said support member for immobilizing biocatalysts;
   circulation means for circulating a nutrient medium between said interior space and said reaction zone and including a circulation pipe comprised of a pipe traversing said intermediate section in axial direction and an extension pipe provided in said interior space of said base and detachably secured to said pipe in said intermediate section, and an agitating means accommodated in said base for circulating the nutrient medium through said circulation pipe; and
   control means arranged in said base for monitoring and controlling conditions in the reactor for each mode of operation of the reactor.

2. A reactor as defined in claim 1 wherein said support member includes a support plate with a hydrophobic surface and a permeability of 3 to 12%.

3. A reactor as defined in claim 2 wherein said support plate has a permeability of 5 to 7.5%.

4. A reactor as defined in claim 1 wherein said gas bubbles-permeable support member is a static mixer for creating an increased oxygen transfer during flow of nutrient medium therethrough.

5. A reactor as defined in claim 1 wherein said pipe in said intermediate section has an open end, and further comprising a grid covering said open end of said pipe in said intermediate section.

6. A reactor as defined in claim 1 wherein said agitating means is an axial-flow pump for directing the nutrient medium in axial direction and including an impeller, said extension pipe having a lower end provided with a collar which surrounds said impeller.

7. A reactor as defined in claim 6, and further comprising a flared transition conically widening toward said collar for connecting said extension pipe with said collar.

8. A reactor as defined in claim 6 wherein said collar defines a central axis, said impeller extending approximately in said axis.

9. A reactor as defined in claim 6, and further comprising baffles accommodated within said collar for preventing a rotation of reactor liquid during rotation of said impeller.

10. A reactor as defined in claim 6 wherein said interior space of said base has an inner wall surface, and further comprising baffles arranged in a space between said collar and said inner wall surface for deflecting reactor liquid vertically upwards to flow evenly through said support member.

11. A reactor as defined in claim 6, and further comprising gas supply means provided in said base and communicating with said circulation pipe above said agitating means.

12. A reactor as defined in claim 7, and further comprising gas supply means provided in said base and communicating with said circulation pipe above said agitating means, said gas supply means being connected to said flared transition.

13. A reactor as defined in claim 6 wherein said impeller includes blades adapted for reducing shear.

14. A reactor as defined in claim 6 wherein said agitating means includes a motor for allowing rotation of said impeller in both directions.

* * * * *